US012751687B2

(12) United States Patent
Siedenburg

(10) Patent No.: US 12,751,687 B2
(45) Date of Patent: Oct. 6, 2026

(54) NON-INVASIVE BLOOD PRESSURE MEASUREMENT DEVICES, SYSTEMS AND METHODS

(71) Applicant: Stryker Corporation, Kalamazoo, MI (US)

(72) Inventor: Clinton T. Siedenburg, Everett, WA (US)

(73) Assignee: Stryker Corporation, Portage, MI (US)

( * ) Notice: Subject to any disclaimer, the term of this patent is extended or adjusted under 35 U.S.C. 154(b) by 484 days.

(21) Appl. No.: 15/999,038

(22) Filed: Aug. 16, 2018

(65) Prior Publication Data

US 2019/0053779 A1 Feb. 21, 2019

Related U.S. Application Data

(60) Provisional application No. 62/547,011, filed on Aug. 17, 2017.

(51) Int. Cl.
*A61B 8/04* (2006.01)
*A61B 5/021* (2006.01)
(Continued)

(52) U.S. Cl.
CPC ............ *A61B 8/04* (2013.01); *A61B 5/02108* (2013.01); *A61B 5/0215* (2013.01);
(Continued)

(58) Field of Classification Search
CPC ..... A61B 8/04; A61B 5/02108; A61B 5/0215; A61B 5/02225; A61B 8/5246; A61B 8/06; A61B 8/0891; A61B 8/485
See application file for complete search history.

(56) References Cited

U.S. PATENT DOCUMENTS 4,336,808 A 6/1982 Ohno et al.
5,249,577 A 10/1993 Shinomura et al.
(Continued)

FOREIGN PATENT DOCUMENTS

EP 0898938 A2 3/1999
WO WO2008050334 A2 5/2008
(Continued)

OTHER PUBLICATIONS

Meinders, J. et al. "Simultaneous assessment of diameter and pressure waveforms in the carotid artery," Ultrasound in Medicine and Biology. 30(2), 2004. p. 147-154 (Year: 2004).*
(Continued)

*Primary Examiner* — Sean A Frith
(74) *Attorney, Agent, or Firm* — Lee & Hayes. P.C.

(57) ABSTRACT

The disclosed non-invasive blood pressure measurement systems and methods using the conservation of mass, conservation of momentum, and/or constitutive equation(s), which may also include the water hammer equation use pulse wave velocity and blood velocity. There are multiple manners by which pulse wave velocity and blood velocity may be assessed by transmitting energy, such as light or ultrasound, through tissues of the patient and measuring values and times of reflectivity of the energy from the interrogated tissues. Blood pressure can be determined from the one or more manners of assessing the PWV, blood velocity, and blood flow profile.

19 Claims, 2 Drawing Sheets

(51) Int. Cl.

| | |
|---|---|
| ***A61B 5/0215*** | (2006.01) |
| ***A61B 5/022*** | (2006.01) |
| ***A61B 8/00*** | (2006.01) |
| ***A61B 8/06*** | (2006.01) |
| ***A61B 8/08*** | (2006.01) |

(52) U.S. Cl.

CPC ........ *A61B 5/02225* (2013.01); *A61B 8/5246* (2013.01); *A61B 8/06* (2013.01); *A61B 8/0891* (2013.01); *A61B 8/485* (2013.01)

(56) References Cited

U.S. PATENT DOCUMENTS

| | | | |
|---|---|---|---|
| 5,309,916 | A | 5/1994 | Hatschek |
| 5,535,747 | A | 7/1996 | Katakura |
| 6,113,539 | A | 9/2000 | Ridenour |
| 6,176,832 | B1 | 1/2001 | Habu et al. |
| 6,261,233 | B1 | 7/2001 | Kantorovich |
| 6,419,632 | B1 | 7/2002 | Shiki et al. |
| 6,676,600 | B1 | 1/2004 | Conero et al. |
| 7,125,383 | B2 | 10/2006 | Hoctor et al. |
| 7,306,563 | B2 | 12/2007 | Huang |
| 7,621,876 | B2 | 11/2009 | Hoctor et al. |
| 7,815,574 | B2 | 10/2010 | Mourad et al. |
| 8,152,732 | B2 | 4/2012 | Lynn et al. |
| 8,187,201 | B2 | 5/2012 | Lynn |
| 8,728,001 | B2 | 5/2014 | Lynn |
| 8,738,128 | B2 | 5/2014 | Pearce et al. |
| 8,932,227 | B2 | 1/2015 | Lynn |
| 9,042,952 | B2 | 5/2015 | Lynn et al. |
| 9,161,701 | B2 | 10/2015 | Lading |
| 9,468,378 | B2 | 10/2016 | Lynn et al. |
| 10,709,424 | B2 | 7/2020 | Joseph et al. |
| 10,722,209 | B2 | 7/2020 | Chen et al. |
| 11,298,103 | B2 | 4/2022 | Weinberg |
| 2002/0177781 | A1 | 11/2002 | Amano |
| 2005/0131282 | A1 | 6/2005 | Brodnick et al. |
| 2005/0143640 | A1 | 6/2005 | Hoctor et al. |
| 2005/0203352 | A1 | 9/2005 | Al-Ali et al. |
| 2005/0228282 | A1 | 10/2005 | Wang et al. |
| 2006/0173514 | A1 | 8/2006 | Biel et al. |
| 2006/0211942 | A1 | 9/2006 | Hoctor et al. |
| 2006/0247701 | A1 | 11/2006 | Zacouto |
| 2007/0010748 | A1 | 1/2007 | Rauch et al. |
| 2007/0060785 | A1 | 3/2007 | Freeman |
| 2007/0093702 | A1 | 4/2007 | Yu et al. |
| 2007/0167844 | A1 | 7/2007 | Asada et al. |
| 2007/0191697 | A1 | 8/2007 | Lynn et al. |
| 2008/0269818 | A1 | 10/2008 | Sullivan et al. |
| 2008/0306354 | A1 | 12/2008 | Mason |
| 2009/0117861 | A1 | 5/2009 | Hoefel et al. |
| 2009/0131805 | A1 | 5/2009 | O'Brien et al. |
| 2009/0270930 | A1 | 10/2009 | Walker et al. |
| 2009/0281838 | A1 | 11/2009 | Lynn et al. |
| 2010/0022886 | A1 | 1/2010 | Ayati et al. |
| 2010/0030020 | A1 | 2/2010 | Sanders et al. |
| 2010/0160778 | A1* | 6/2010 | Eskandari ........... G01S 15/8977 600/438 |
| 2010/0176952 | A1 | 7/2010 | Bajcsy et al. |
| 2010/0217102 | A1 | 8/2010 | LeBoeuf et al. |
| 2011/0009711 | A1 | 1/2011 | Nanikashvili et al. |
| 2011/0040197 | A1 | 2/2011 | Welch et al. |
| 2011/0130669 | A1 | 6/2011 | Garner et al. |
| 2012/0016179 | A1 | 1/2012 | Paradis et al. |
| 2012/0123246 | A1 | 5/2012 | King et al. |
| 2012/0245439 | A1 | 9/2012 | Andre et al. |
| 2013/0178736 | A1* | 7/2013 | Pahlevan ............... A61B 5/021 600/430 |
| 2013/0276785 | A1 | 10/2013 | Melker et al. |
| 2013/0303923 | A1* | 11/2013 | Lerner ............... A61B 5/02208 600/490 |
| 2013/0345573 | A1 | 12/2013 | Kargar et al. |
| 2014/0143064 | A1* | 5/2014 | Tran ....................... A61B 5/747 705/14.66 |
| 2014/0152673 | A1 | 6/2014 | Lynn et al. |
| 2014/0163897 | A1 | 6/2014 | Lynn et al. |
| 2014/0200423 | A1 | 7/2014 | Eisen et al. |
| 2014/0288953 | A1 | 9/2014 | Lynn et al. |
| 2014/0296675 | A1 | 10/2014 | Freeman et al. |
| 2014/0324763 | A1 | 10/2014 | Lurie et al. |
| 2014/0365175 | A1 | 12/2014 | Packer et al. |
| 2015/0045686 | A1 | 2/2015 | Lynn |
| 2015/0073230 | A1 | 3/2015 | Stergiou |
| 2015/0087936 | A1 | 3/2015 | Al-Ali et al. |
| 2015/0105636 | A1 | 4/2015 | Hayman et al. |
| 2015/0105637 | A1 | 4/2015 | Yu et al. |
| 2015/0169835 | A1 | 6/2015 | Hamdan et al. |
| 2015/0238095 | A1* | 8/2015 | Lading ................. A61B 5/0285 600/410 |
| 2015/0327785 | A1 | 11/2015 | Lading et al. |
| 2015/0327786 | A1 | 11/2015 | Lading et al. |
| 2016/0007862 | A1 | 1/2016 | Ku |
| 2016/0030758 | A1 | 2/2016 | Guiney et al. |
| 2016/0038117 | A1 | 2/2016 | Tamada |
| 2016/0054354 | A1 | 2/2016 | Keal et al. |
| 2016/0067499 | A1 | 3/2016 | Owen et al. |
| 2016/0095572 | A1* | 4/2016 | Aguren .................... A61B 8/04 600/438 |
| 2016/0135706 | A1 | 5/2016 | Sullivan et al. |
| 2016/0199029 | A1 | 7/2016 | Struijk et al. |
| 2016/0199251 | A1 | 7/2016 | Aelen et al. |
| 2016/0256350 | A1 | 9/2016 | Johnson et al. |
| 2016/0262639 | A1 | 9/2016 | Ukawa |
| 2016/0270673 | A1 | 9/2016 | Aelen et al. |
| 2016/0287095 | A1 | 10/2016 | Gu |
| 2016/0317385 | A1 | 11/2016 | Salcido et al. |
| 2016/0345930 | A1 | 12/2016 | Mizukami et al. |
| 2017/0000688 | A1 | 1/2017 | Kaufman et al. |
| 2017/0042504 | A1* | 2/2017 | Rich ........................ A61B 8/04 |
| 2017/0065484 | A1 | 3/2017 | Addison et al. |
| 2017/0079530 | A1 | 3/2017 | DiMaio et al. |
| 2017/0105644 | A1 | 4/2017 | Sullivan et al. |
| 2017/0105898 | A1 | 4/2017 | Taylor et al. |
| 2017/0120063 | A1 | 5/2017 | Freeman et al. |
| 2017/0156706 | A1 | 6/2017 | Joseph et al. |
| 2017/0172429 | A1 | 6/2017 | Takoh et al. |
| 2017/0181925 | A1 | 6/2017 | Oppenheimer et al. |
| 2017/0209053 | A1 | 7/2017 | Pantelopoulos et al. |
| 2017/0231598 | A1 | 8/2017 | Baek et al. |
| 2017/0238817 | A1* | 8/2017 | Lading ................. A61B 5/6824 |
| 2017/0251930 | A1 | 9/2017 | Machida et al. |
| 2017/0251936 | A1 | 9/2017 | Sawado et al. |
| 2017/0266399 | A1 | 9/2017 | Campana et al. |
| 2017/0273664 | A1 | 9/2017 | Baym et al. |
| 2017/0354331 | A1 | 12/2017 | Borkholder et al. |
| 2017/0360313 | A1 | 12/2017 | Baek et al. |
| 2017/0367618 | A1 | 12/2017 | Ricciardelli et al. |
| 2018/0040255 | A1 | 2/2018 | Freeman et al. |
| 2018/0078155 | A1 | 3/2018 | Baek et al. |
| 2018/0110667 | A1 | 4/2018 | Freeman et al. |
| 2018/0125430 | A1 | 5/2018 | Al-Ali et al. |
| 2018/0153765 | A1 | 6/2018 | Freeman et al. |
| 2018/0199834 | A1 | 7/2018 | Siedenburg |
| 2018/0200142 | A1 | 7/2018 | Freeman et al. |
| 2018/0206746 | A1 | 7/2018 | Narasimhan et al. |
| 2018/0206795 | A1 | 7/2018 | Al-Ali |
| 2018/0224534 | A1 | 8/2018 | Schulte |
| 2018/0235567 | A1 | 8/2018 | Bezemer et al. |
| 2018/0256043 | A1 | 9/2018 | Melker |
| 2018/0303411 | A1 | 10/2018 | Walker et al. |
| 2018/0369065 | A1 | 12/2018 | Siedenburg et al. |
| 2019/0008432 | A1 | 1/2019 | Bashan et al. |
| 2019/0014997 | A9 | 1/2019 | Siedenburg |
| 2019/0053779 | A1 | 2/2019 | Siedenburg |
| 2019/0099153 | A1 | 4/2019 | Weinberg |
| 2019/0125191 | A1 | 5/2019 | Siedenburg |
| 2019/0175035 | A1 | 6/2019 | Van Der Horst |
| 2019/0270673 | A1 | 9/2019 | Nakamoto et al. |
| 2019/0380597 | A1 | 12/2019 | Howard |
| 2021/0275131 | A1 | 9/2021 | Siedenburg et al. |
| 2022/0061684 | A1 | 3/2022 | Siedenburg |
| 2022/0369942 | A1 | 11/2022 | Siedenburg |

(56) References Cited

U.S. PATENT DOCUMENTS

2023/0043552 A1 2/2023 Siedenburg
2024/0206746 A1 6/2024 Siedenburg
2026/0026775 A1 1/2026 Siedenburg

FOREIGN PATENT DOCUMENTS

WO WO2016081517 A2 5/2016
WO WO2017032648 A1 3/2017
WO WO2017115361 A1 7/2017

OTHER PUBLICATIONS

Messas, M., et al. "Arterial wall elasticity: state of the art and future prospects," Diagnostic and Interventional Imaging, 2013. p. 561-569 (Year: 2013).*
Hoeks et al. "Non-invasive measurement of mechanical properties of arteries in health and disease", Proceedings of the Institution of Mechanical Engineers, Part H: Journal of Engineering in Medicine, 1999. Vol 213 Part H, p. 195-202. (Year: 1999).*
Bernal, M., et al. "Material property estimation for tubes and arteries using ultrasound radiation force and propagating modes," Acoustical Society of America. Vol 129(3), 2011. p. 1344-1354 (Year: 2011).*
Qi, W., et al., "Phase-resolved acoustic radiation force optical coherence elastography," Journal of Biomedical Optics. Vol 17(11), 2012. p. 110505-1-110505-3 (Year: 2012).*
Bercoff, J., et al. "Supersonic Shear Imaging: A New Technique for Soft Tissue Elasticity Mapping," IEEE Transactions on Ultrasonics, Ferroelectrics, and Frequency control. vol. 51(4), 2004. p. 396-409 (Year: 2004).*
Rabben, S., et al. "An ultrasound-based method for determining pulse wave velocity in superficial arteries," Journal of Biomechanics. vol. 37, 2004. p. 1615-1622 (Year: 2004).*
Montaldo, G., et al. "Ultrafast Compound Doppler Imaging: A New Approach of Doppler Flow Analysis," IEEE ISBI 2010. 2010. p. 324-327 (Year: 2010).*
Jensen, J. "Comparison of Vector Velocity Imaging using Directional Beamforming and Transverse Oscillation for a Convex Array Transducer," SPIE Medical Imaging San Diego, 2014. p. 904012-1-904012-8 (Year: 2014).*
Bank, A., et al., "In Vivo Brachial Artery Elastic Mechanics Effects of Smooth Muscle Relaxation," Circulation Journal of the American Heart Association. vol. 100(1), 1999. p. 41-47 (Year: 1999).*
Lin, A., et al. "Circumferential Strain in the Wall of the Common Carotid Artery: Comparing Displacement-Encoded and Cine MRI in Volunteers," Magnetic Resonance Medicine. vol. 60(1), 2008. p. 8-13 (Year: 2008).*
Soleimani, E., et al., "Assessing the blood pressure waveform of the carotid artery using an ultrasound image processing method," Ultrasonography. vol. 36, Apr. 2017. p. 144-152 (Year: 2017).*
Genovese, M., "Ultrasound Transducers," Journal of Diagnostic Medical Sonography. vol. 32, 2016. p. 48-53 (Year: 2016).*
Nightingale, K., "Acoustic Radiation Force Impulse (ARFI) Imaging: A Review" Curr Med Imaging Rev. vol. 7(4), 2011. p. 328-339 ( Year: 2011).*
U.S. Appl. No. 16/103,797, filed Aug. 14, 2018, titled "Constitutive Equation for Non-Invasive Blood Pressure Measurement Systems and Methods".
Beulen, et al., "Toward Noninvasive Blood Pressure Assessment in Arteries by Using Ultrasound", Ultrasound in Med. & Biol., vol. 37, No. 5, Mar. 2011, pp. 788-797.
European Office Action mailed Jan. 12, 2021 for European Patent Application No. 18703419.4, a counterpart foreign application of U.S. Appl. No. 15/874,796, 5 pages.
International Search Report & Written Opinion, dated Jan. 25, 2018; International Application No. PCT/US2017/60708, filed Nov. 8, 2017; 9 pages.
International Search Report & Written Opinion, dated Apr. 17, 2018; International Application No. PCT/US2018/014273, filed Jan. 18, 2018; 14 pages.
Murgo et al. "Aortic Input Impedance in Normal Man: Relationship to Pressure Wave Forms", American Heart Association, Circulation, vol. 62, No. 1, Jul. 1980, pp. 105-116.
O'Rourke, "Vascular Impedance in Studies of Arterial and Cardiac Function", School of Medicine, Univ. of New South Wales, St. Vincent's Hospital, Sydney, AU, Physiological Reviews, vol. 62, No. 2, Apr. 1982, pp. 570-623.
Office Action for U.S. Appl. No. 15/874,796, mailed on Jan. 28, 2021, Siedenburg, "Non-Invasive Blood Pressure Measurement Using Pulse Wave Velocity", 38 pages.
Office Action for U.S. Appl. No. 16/103,797, mailed on Apr. 28, 2021, Siedenburg, "Constitutive Equation for Non-Invasive Blood Pressure Measurement Systems and Methods", 16 pages.
Office Action for U.S. Appl. No. 16/167,195, mailed on Jun. 4, 2021, "Light-Based Non-Invasive Blood Pressure Systems and Method", 12 pages.
Office Action for U.S. Appl. No. 15/874,796, mailed on Sep. 1, 2020, Siedenburg, "Non-Invasive Blood Pressure Measurement Using Pulse Wave Velocity", 39 pages.
Office Action for U.S. Appl. No. 16/103,797, mailed on Dec. 16, 2020, Siedenburg, "Constitutive Equation for Non-Invasive Blood Pressure Measurement Systems and Methods", 16 pages.
Office Action for U.S. Appl. No. 16/167,195, mailed on Feb. 1, 2021, Siedenburg, "Light-Based Non-Invasive Blood Pressure Systems and Method", 10 pages.
Pereira et al., "Novel Methods for Pulse Wave Velocity Measurement", Physics Dept. Instrumentation Center, Univ. of Coimbra, Rua Larga, Coimbra, PT. J. Med Biol. Eng., Oct. 2015, 555-565.
Rajan, et al., "Review of methodological developments in laser Doppler flowmetry," Lasers Med Sci, 24:269-283, Mar. 2009.
Soleimani et al. "Assessing the Blood Pressure Waveform of the Carotid Artery Using an Ultrasound Image Processing Method", Univ. of Tehran, IR, Ultrasonography, Apr. 2017, pp. 144-152.
Struijk et al. "Blood Pressure Estimation in the Human Fetal Descending Aorta", Wiley InterScience, Ultrasound Obstet Gynecol, Sep. 2008, pp. 673-681.
Tijsseling, et al., "Johannes von Kries and the History of Water Hammer", Journal of Hydraulic Engineering—ASCE, vol. 133, Jan. 2007, 9 pages.
Vennin et al., "Noninvasive calculation of the aortic blood pressure waveform from the flow velocity waveform: a proof of concept", Am J Physiol Heart Circ Physiol 309: H969-H976, Jul. 2015.
European Communication Pursuant to Article 94(3) EPC mailed Sep. 26, 2022 for European Application No. 18703419.4, a counterpart foreign application of U.S. Appl. No. 15/874,796, 6 pages.
Office Action for U.S. Appl. No. 17/521,734, mailed on Mar. 3, 2023, Clinton T. Siedenburg, "Non-Invasive Blood Pressure Measurement Using Pulse Wave Velocity", 24 pages.
Office Action for U.S. Appl. No. 17/521,734, mailed on Jun. 27, 2023, Siedenburg, "Non-Invasive Blood Pressure Measurement Using Pulse Wave Velocity", 11 Pages.
Office Action for U.S. Appl. No. 17/888,031, mailed on Sep. 14, 2023, Clinton T. Siedenburg, "Constitutive Equation for Non-Invasive Blood Pressure Measurement Systems and Methods", 18 pages.
Williams, et al., "Noninvasive Ultrasonic Measurement of Regional and Local Pulse-Wave Velocity in Mice", Ultrasound in Medicine & Biology, vol. 33, No. 9, 2007, pp. 1368-1375.
Office Action for U.S. Appl. No. 17/888,031, mailed on Mar. 15, 2023, Siedenburg, "Constitutive Equation for Non-Invasive Blood Pressure Measurement Systems and Methods", 20 pages.
Office Action for Canadian Application No. 3,050,694, dated Feb. 20, 2024, 4 pages.
Office Action for U.S. Appl. No. 17/838,128, mailed on Mar. 7, 2024, Siedenburg, "Light-Based Non-Invasive Blood Pressure Systems and Methods," 10 pages.
Office Action for U.S. Appl. No. 17/888,031, mailed on Apr. 8, 2024, Siedenburg, "Constitutive Equation for Non-Invasive Blood Pressure Measurement Systems and Methods," 19 pages.

(56) References Cited

OTHER PUBLICATIONS

Office Action for U.S. Appl. No. 16/167,195, mailed on Sep. 13, 2021, Siedenburg, "Light-Based Non-Invasive Blood Pressure Systems and Method", 13 pages.
Elola, et al., "Capnography: A support tool for the detection of return of spontaneous circulation in out-of-hospital cardiac arrest," Resuscitation, Sep. 2019, pp. 153-161.
Feng, et al., "Determination of wave speed and wave separation in the arteries using diameter and velocity", Journal of Biomechanics, vol. 43, (2010), Feb. 10, 2010, pp. 455-462.
Nagahara, et al., "In Vivo Measurement of Blood Velocity in Human Major Retinal Vessels Using the Laser Speckle Method," Retina, Investigative Ophthalmology & Visual Science, vol. 52, No. 1, Jan. 2011, pp. 87-92.
Pomella, et al., "Common Carotid Artery Diameter, Blood Flow Velocity and Wave Intensity Responses at Rest And During Exercise in Young Healthy Humans: A Reproducibility Study", Ultrasound in Medicine & Biololgy, vol. 43, No. 5, May 2017, pp. 943-957.
Rader, et al., "An Interferometric Blood Flow Measurement Technique - A Brief Analysis," IEEE Transactions on Biomedical Engineering, vol. BME-21, No. 4, Jul. 1974, pp. 293-297.
Robinson, et al., "Portable, High Speed Blood Flow Measurements Enabled by Long Wavelength, Interferometric Diffuse Correlation Spectroscopy (LW-iDCS)," Scientific Reports vol. 13, Article No. 8803 (2023), May 2023, pp. 1-11.

* cited by examiner

NON-INVASIVE BLOOD PRESSURE MEASUREMENT DEVICES, SYSTEMS AND METHODS

CROSS-REFERENCE TO RELATED APPLICATIONS

This patent application claims the benefit of and priority to U.S. Provisional Patent Application Ser. No. 62/547,011, filed on Aug. 17, 2017, entitled "NIBP Using Ultrasound in Other Ways," the contents of which are hereby incorporated by reference in their entirety.

This application is related to U.S. patent application Ser. No. 15/874,796, filed Jan. 18, 2018, entitled "Non-Invasive Blood Pressure Measurement Using Pulse Wave Velocity," and U.S. patent application Ser. No. 16/103,797, filed Aug. 14, 2018, entitled "Constitutive Equation for Non-Invasive Blood Pressure Measurement Systems and Methods," the contents of which are hereby incorporated by reference in their entirety.

BACKGROUND

The blood pressure of a patient is a critical measurement that is used in monitoring and treating the patient. There are two means by which the blood pressure of the patient can be measured—one is invasive and the other is non-invasive. In the invasive means, the blood pressure is obtained by direct measurement, requiring a sensor to be inserted into the circulatory system of the patient to obtain the measurements. As such, the invasive means, while providing an accurate measurement, can cause discomfort in the patient or the subject for which the blood pressure is being measured. Additionally, there is an increased risk of complications and/or expense due to the invasive nature of such blood pressure measurement. Such increased complications risk and/or expenses can be unwarranted in many cases, such as during a simple patient examination.

In the non-invasive means, the sensing of the blood pressure is done externally to the patient. Typically, this involves the application of a cuff about a limb of the patient and the pressurization of the cuff to cut off circulation through the limb. The pressure applied by the cuff to the limb is slowly reduced and as blood flow is resumed, the blood pressure can be measured based on the pressure remaining in the cuff. This process is often repeated multiple times to monitor blood pressure, with pauses required between measurement instances. While this means is non-invasive, it does require the temporary cessation of circulation in a portion of the patient, which can be uncomfortable or damaging to the health of the patient and requires time for the process to be fully performed. Additionally, such non-invasive blood pressure measurement techniques are sensitive to motion of the patient and equipment, which can result in inaccurate and/or unobtainable blood pressure measurements. In patient transport or emergency situations, the patient and equipment can be subjected to a large amount of motion during time in which an accurate blood pressure measurement can be critical to assess the state of the patient.

Blood pressure measurement and/or monitoring can be improved by non-invasive blood pressure systems and/or methods that do not require the restriction of circulation and provides the accurate blood pressure values/measurements needed for patient treatment and/or monitoring.

DETAILED DESCRIPTION

The disclosed devices, systems and methods non-invasively determine, measure and/or calculate a blood pressure of a patient. Data and/or measurements of the patient's blood flow and vessel, or vascular, structures are obtained in a non-invasive manner and are used to calculate at least one of a pulse wave velocity (PWV), blood velocity, blood flow profile and/or vessel geometry. These values are then used to calculate a blood pressure of the patient using the conservation of mass, the conversation of momentum, or the constitutive equation and/or water hammer equation, such as described in related U.S. patent application Ser. No. 15/874,796 and U.S. patent application Ser. No. 16/103,797, the contents of which are both incorporated by reference. In an example, energy, such as ultrasound or light, can be transmitted through the tissues of a patient. The energy will reflect from the tissues based on their reflectivity and the reflected energy can be received and used to calculate the various values/geometries, which can be used to calculate a blood pressure of the patient. The calculated/determined blood pressure can be used to provide blood pressure data to one or more devices, systems and/or users, such as for the treatment and/or monitoring of the patient.

Figure 1:
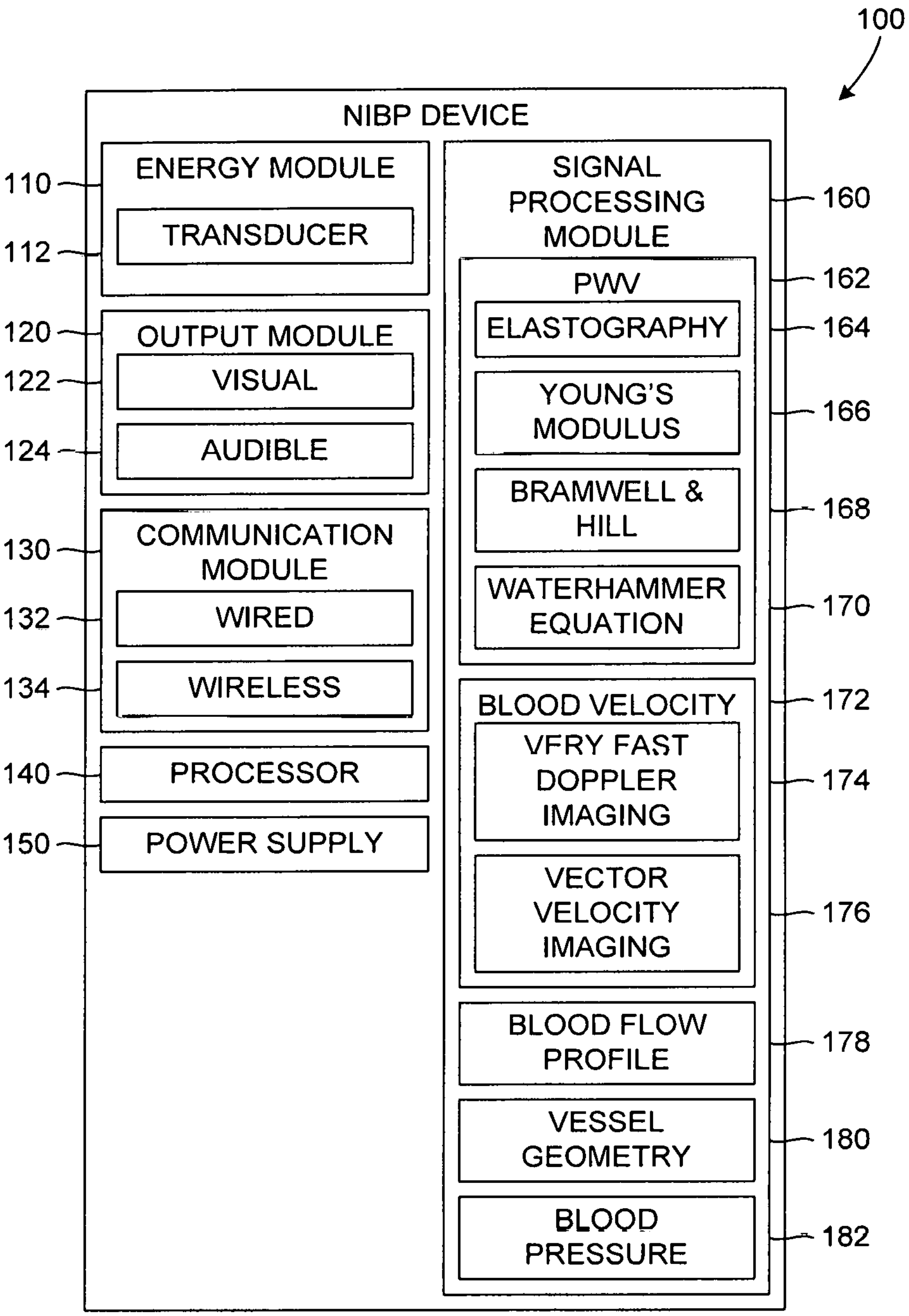
FIG. 1 is an example non-invasive blood pressure device.

FIG. 1 illustrates an example non-invasive blood pressure (NIBP) device 100. The NIBP device includes an energy module 110, an output module 120, a communication module 130, a processor 140, a power supply 150 and a signal processing module 160. In one example, the energy module 110 can be an ultrasound module although it could be a module that emits other forms of energy as well, such as light, for example. Using the ultrasound energy embodiment as an example here, the NIBP device can be placed on a patient to emit ultrasound energy into tissues of the patient. The ultrasound energy will transmit through the tissues of the patient and will reflect therefrom. The reflected ultrasound energy will have characteristics, such as a power level, Doppler shift, and/or other characteristics, based on the reflectivity of the tissues which is caused by an impedance change in the reflected signal due to the density of the tissues through which the ultrasound energy transmits and/or change in the speed of the ultrasound energy during transit through the tissues. The reflected energy can be processed to generate measurements and/or calculations of various patient physiological parameters, including a blood pressure of the patient.

The ultrasound module 110 includes one or more transducers 112 which output ultrasound energy in response to an applied electrical signal and output an electrical signal in response to received energy, such as reflected ultrasound energy. The electrical signal applied to the transducer(s) 112 can cause the ultrasound energy emitted by the transducer(s) 112 to have various properties/characteristics, such as a wavelength, frequency, intensity, waveform and/or other properties/characteristics. The received reflected ultrasound energy causes the transducer(s) 112 to generate an electrical signal, such as a reflected energy signal, that can be processed, such as by the signal processing module 160, to measure/calculate one or more patient physiological characteristics/measurements.

In an example, the ultrasound module 110 can include multiple transducers 112. The transducers 112 can be arranged, such as in an array, and/or coordinated to emit and/or receive ultrasound energy in a desired, or required, manner. Additionally, the transducers 112 can be interconnected by various switching elements to control the emission and/or reception of ultrasound energy by the transducers 112.

The output module 120 can include a visual 122 and/or an audible output 124. The visual 122 and/or an audible output 124 can be used to provide information, such as a calculation, alert and/or other information, from the NIBP device 100 to a user or other device. The visual output 122 can include a screen, lights and/or other visible outputs that can provide visually interpretable/receivable information to the user or other device. The audible output 124 can include a speaker, buzzer, annunciator and/or other audible outputs that can provide audibly interpretable/receivable information to the user or other device.

The communication module 130 can provide communication from, to and/or between the NIBP device 100 and an external device and/or system, such as a mobile computing device, a patient monitoring system and/or other devices/systems remote from and/or coupled to the NIBP device 100. The communication can be through a connection, such as a wired 132 and/or a wireless connection 134. The wired connection 132 can include a physical connection between and capable of providing communication from, to and/or between the NIBP device 100 and another device/system, such as a wire(s). The wireless connection 134 can include a wireless connection between and capable of providing communication from, to and/or between the NIBP device 100 and another device/system, such as a network, WAN, LAN, Wi-Fi, Bluetooth®, and/or other wireless connection. Communication from the NIBP device 100, to another device/system, can include calculation and/or measured data, an operating status of the NIBP device 100 and/or other information from, or regarding, the NIBP device 100. Communication to the NIBP device 100, from another device/system, can include operating instructions/commands, data from an external source and/or other information to the NIBP device 100.

The processor 140 can assist, and/or control operation of, one or more of the modules of the NIBP device 100, such as the ultrasound module 110, the output module 120, communication module 130 and signal processing module 160. In an example, the processor 140 can be accessed by the signal processing module 160, and/or included therein, to assist with processing the reflected energy signal from the ultrasound module 110. Alternatively, or additionally, the processor 140 can control operation of the NIBP device 100, such as in response to an input by a user, device and/or system. Inputs by a user can be received through an interface of the NIBP device 100, such as a button or touchscreen, and/or through an interface on an external device/system in communication with, or coupled to, the NIBP device 100, such as through an application on the external device/system.

The power supply 150 can provide, and/or distribute, power to the various functions and/or features of the NIBP device 100. In an example, the power supply can be an energy storage device, such as a battery, that can be rechargeable, replaceable, removable and/or permanent. Alternatively, or additionally, the power supply 150 can include a physical connection that can be connected to an external power source, such as a wall outlet or another device/system, to provide power to the various functions and/or features of the NIBP device 100.

The signal processing module 160 can receive and process the reflected energy signal from the ultrasound module 110 to measure/calculate a pulse wave velocity (PWV)

parameters 162, blood velocity parameters 172, blood flow profile parameters 178, vessel geometry parameters 180, and/or a blood pressure 182. Alternatively, the reflected energy signal, or data, can be communicated to another device/system, which can process the reflected energy to calculate/determine one or more of the values. The NIBP device 100 can measure/calculate the blood pressure of a patient, in a non-invasive manner, using one or more of the measured/calculated parameters of the PWV 162, blood velocity 172, blood flow profile 178 and/or vessel geometry 180. To measure/calculate the blood pressure, the NIBP device 100 can use a constitutive equation and/or water hammer equation that relates the one or more measured/calculated parameter to a blood pressure of the patient.

Pulse wave velocity (PWV) 162 is a measure of the velocity of an arterial pressure pulse as it travels through the circulatory system of a patient. A simple measurement of a distance the pulse travels in a measured amount of time can be used to determine PWV, however, this requires tracking the propagation of the pulse wave between two fixed points having a known distance between them. In another method, PWV can be measured at a single location using a variety of factors, such as various vessel geometry measurements obtained/determined with respect to time and assumptions regarding the flow of blood through a circulatory system. Described below are other methods/calculations for determining/calculating/measuring the PWV using ultrasound or light.

A first manner can include direct measurements using elastography 164. Ultrasound shear wave imaging techniques can be used to image the motion of the vessel, or tissues, as the pulse wave propagates through. Using this data, the speed of the pulse wave can be calculated/determined. The PWV data can then be used, such as in the constitutive equation and/or the waterhammer equation, to calculate a blood pressure of a patient.

In a second manner, a direct measurement of the Young's modulus 166 of a vessel can be made. The Moens-Kortweg equation (Equation 1), shown below, relates PWV to the Young's modulus (E(x)) 166, wall thickness (h(x)), vessel radius ($R_0(x)$) and density (ρ). Both the wall thickness (h(x)) and vessel radius ($R_0(x)$) can be measured/calculated using one or more ultrasound techniques and the density (ρ) can be a known, or an assumed, value of the density of blood. Young's modulus 166 can also be measured, or calculated, and used with the other values to calculate PWV, as shown below.

$$PWV = \sqrt{\frac{E(x)h(x)}{2R_0(x)\rho}} \qquad \text{Equation 1}$$

Young's modulus, E(x), is defined as stress over strain and can be expressed in terms of tensile stress (Force/unit area) and strain (relative elongation), as shown in Equation 2, below:

$$E \equiv \frac{\frac{F}{A}}{\frac{\Delta L}{L_0}} \qquad \text{Equation 2}$$

To calculate the Young's modulus 166 using ultrasound, the transducers 112 can be controlled to emit acoustic radiation force imaging (ARFI) pulses, often used in ultrasound for high frame rate shear wave imaging, such as used in ultrasound elastography, to apply pressure on the vessel to "push" the vessel using acoustic, or ultrasound, energy. The amount, or magnitude, of force (F) applied to the vessel by this imaging technique can be estimated by correlating it to movement observed in the surrounding tissues using speckle tracking, the magnitude of reflection and/or a calculation. To determine the area (A) over which the force is applied, an estimation can be made from the beam pattern computations regarding the emitted ultrasound energy and/or a calculation/measurement can be made from measurements of the tissue movement using speckle tracking. The force applied to the vessel using ultrasound can be emitted from a single direction and/or from multiple directions simultaneously. Alternatively, or additionally, the force to the vessel can be applied in other means, such as by palpation of the vessel, and measurements/estimates/calculations of the applied force can be made using the above-described, or other, ultrasound techniques, as well as other non-ultrasound techniques such as light, pressure or motion sensors.

The strain of the vessel is measured as distention of the vessel, that is, an increasing radius of the vessel compared to a previous, or static, radius measurement. Ultrasound technique(s) can be used to measure, or calculate, the change in circumference of the vessel and/or a change in a length of a portion of the circumference of the vessel. When measuring a change in length of a portion of the circumference, the portion being measured is the same portion to which the force is being applied. The strain can then be calculated by dividing the measured/determined change in circumferential length by a known original length.

With both stress and strain of the vessel, or portion thereof, known, the Young's modulus 166 can be calculated using Equation 2. With the Young's modulus 166 measured/calculated/determined, the PWV can be calculated using Equation 1.

Alternatively, ultrasound shear wave imaging, such as described with regards to elastography, can be used to indirectly measure the Young's modulus 166 of the vessel. The shear wave speed is related to the Young's modulus 166 of the vessel and using the measured/known/calculated shear wave speed, the Young's modulus 166 can be computed, tabulated and/or correlated using empirical data.

In a further alternative, the use of AFRI pulses will cause surface waves on the vessel wall, these waves can be measured and are a function of the stiffness of the vessel. As such, these measured values can be correlated, such as by an equation or look-up table, to a Young's modulus 166 of the vessel.

In a further alternative for approximately linear elastic materials, Young's modulus can be computed by simple relationships of at least two other mechanical properties such as bulk modulus, Poison's ratio, Lame parameters, P-wave and S-wave velocities, etc. Measurement of these other mechanical properties may be made using imaging techniques.

In a third manner, the PWV can be computed using the Bramwell-Hill equation 168, Equation 3, shown below:

$$PWV = \sqrt{\frac{dPV}{\rho dV}} \quad \text{Equation 3}$$

Equation 3 relates PWV to pressure (P), volume (V) and density (ρ). A conservation of momentum equation, Equation 4 below, can be used to equate the partial derivatives of the pressure with respect to the dimension of the vessel axis to time and spatial partials of the blood flow.

$$\frac{\partial P}{\partial x}\frac{1}{\rho} = -\left(\frac{\partial U}{\partial t} + (2\alpha - 1)U\frac{\partial U}{\partial x} + (\alpha - 1)\frac{U^2}{A}\frac{\partial A}{\partial x} + 2(\zeta + 2)\frac{\mu\pi U}{\rho A}\right) \quad \text{Equation 4}$$

In Equation 4, U represents flow, a represents Coriolis coefficients and ζ represents a flow profile constant as describe in later equations. Equation 4 is used as the first factor dP/ρ of Equation 3 by interpreting dP as a partial with respect to axial distance.

Volume is simply related to area times length, as shown in Equation 5 below where Δx is an arbitrary, fixed length of vessel.

$$V(x,t) = A(x,t)\Delta x \quad \text{Equation 5}$$

The partial with respect to distance can be expressed as Equation 6, below, noting that Δx is a constant with respect to the partial derivative.

$$\frac{\partial V(x, t)}{\partial x} = \frac{\partial A(x, t)}{\partial x}\Delta x \quad \text{Equation 6}$$

Using Equations 4-6, the various values necessary for Equation 3 can be calculated/determined to solve for PWV as shown in equation 7 interpreting the differentials of Equation 3 as a ratio of partials with respect to the axial dimension.

$$PWV = \sqrt{-\left(\begin{array}{c}\frac{\partial U}{\partial t} + (2\alpha - 1)U\frac{\partial U}{\partial x} + \\ (\alpha - 1)\frac{U^2}{A}\frac{\partial A}{\partial x} + 2(\zeta + 2)\frac{\mu\pi U}{\rho A}\end{array}\right)\left(\frac{A(x, t)}{\frac{\partial A(x, t)}{\partial x}}\right)} \quad \text{Equation 7}$$

When the center terms containing partials with respect to x are small compared to other terms, then PWV can be simplified as Equation 8:

$$PWV = \sqrt{-\left(\frac{\partial U}{\partial t} + 2(\zeta + 2)\frac{\mu\pi U}{\rho A}\right)\left(\frac{A(x, t)}{\frac{\partial A(x, t)}{\partial x}}\right)} \quad \text{Equation 8}$$

The various values necessary for use in these equations, such as blood velocity and geometrical dimensions of the vessel, can be measured/determined using ultrasound techniques.

In a fourth manner, PWV can be calculated using the water hammer equation 170, Equation 9, shown below. Equation 9 includes simultaneous considerations of conservation of mass and momentum.

$$dP(x,t) = -\rho PWC\, dU(x,t) \quad \text{Equation 9}$$

Equation 9 an be divided by a vessel segment length, Δx, to create Equation 10, below.

$$\frac{\Delta P(x,t)}{\Delta x} = -PWV\frac{\Delta U(x,t)}{\Delta x} \quad \text{Equation 10}$$

The left hand side of Equation 10 is equivalent to Equation 4, which contains values measureable using ultrasound techniques. Similarly, $$\frac{\Delta U(x,t)}{\Delta x}$$

is a measurable value of the change in flow, U, with respect to the segment length and time. Density (ρ) is a known value and the terms of Equation 10 can be rewritten so that PWV is expressed in known and measurable values, as shown in Equation 11 below.

Equation 11

$$PWV = \frac{\left(\frac{\Delta P(x,t)}{\Delta x}\right)}{\left(\rho\frac{\Delta U(x,t)}{\Delta x}\right)} = \frac{\left(\frac{\partial U}{\partial t} + (2\alpha-1)U\frac{\partial U}{\partial x} + (\alpha-1)\frac{U^2\partial A}{A\partial x} + 2(\zeta+2)\frac{\mu\pi U}{\rho A}\right)}{\left(\frac{\Delta U(x,t)}{\Delta x}\right)}$$

The measurable values can be taken/made as averages across the cross-sectional area of the vessel to assist with simplification of the calculation with minimal impact to the accuracy of the calculated PWV value and later blood pressure.

Using one or more of the above equations, the PWV value can be determined and used in blood pressure calculations, such as the constitutive equation and/or water hammer equation, to calculate/determine a blood pressure of a patient.

Blood velocity 172 can be calculated and/or measured in a variety of manners. Typical manners can include the use of pulse wave Doppler (PWD) or continuous wave Doppler (CWD) ultrasound imaging techniques. Described below are other manners of calculating/determining blood velocity 172 using measured/calculated values, obtained using one or more ultrasound techniques.

In a first manner, the blood velocity 172 can be determined/calculated using very fast Doppler imaging 174. Plane wave isonification, from one or more angles, can be performed and a times series of data associated with each ultrasound element, such as a transducer 112, can be collected. The collected time series data can then be beamformed to provide an improved/increased frame rate for the given region of interest. The increased frame rate provides enhanced temporal resolution from which derivatives with respect to time can be made/calculated to determine/calculate the blood velocity 172.

In a second manner, vector velocity imaging, or speckle tracking, 176 can be used to calculate/determine the blood velocity 172. The reflection coefficient of blood cells can be imaged using B-mode ultrasound methods. The reflection of ultrasound energy from the blood cells causes moving speckles in the ultrasound image. These speckles can be tracked to determine a velocity of the speckle, or blood cell. The various speckles can be tracked with respect to a frame rate, i.e. time. Using the frame rate and tracking of the speckles, a vector velocity profile can be calculated/determined. Alternatively, or additionally, directional beamforming, synthetic aperture flow imaging and/or transverse oscillations can be used to perform vector velocity imaging 176 using ultrasound.

The Coriolis coefficient, α, of Equation 4, can be calculated/determined using ultrasound imaging/measurement techniques of the blood flow velocity profile in the radial direction. The Coriolis coefficient can be expressed as Equation 12, below.

$$\alpha(x,t) = \frac{1}{AU^2}\int_A U^2 d\sigma \quad \text{Equation 12}$$

In Equations 4, 7, 8 and 11, U is flow and A is cross-sectional area of the vessel. The integration of the flow across the cross-sectional area provides more accurate information than using an assumed average flow. Additionally, this method also allows for the value of the flow profile constant, ζ, to be calculated/determined, such as by using Equation 13, below.

$$\zeta = \frac{2-\alpha}{\alpha-1} \quad \text{Equation 13}$$

The signal processing module 160 can also calculate one or more vessel geometry 180 characteristics, such as the cross-sectional area, radius, circumference and/or other geometric characteristics of the interrogated vessel. These vessel geometry measurements can be used in conjunction with one or more of the above equations/relationships to calculate/determine values, such as the PWV 162, blood velocity 172 and/or blood flow profile 178.

Using the one or more methods/equations described above, one or more values of the PWV 162, blood velocity 172, blood flow profile 178 and/or vessel geometry 180 can be calculated/determined. The one or more values can be used together, alone and/or with other information to calculate/determine a blood pressure 182 of the patient, such as by using a constitutive equation and/or water hammer equation.

Figure 2:
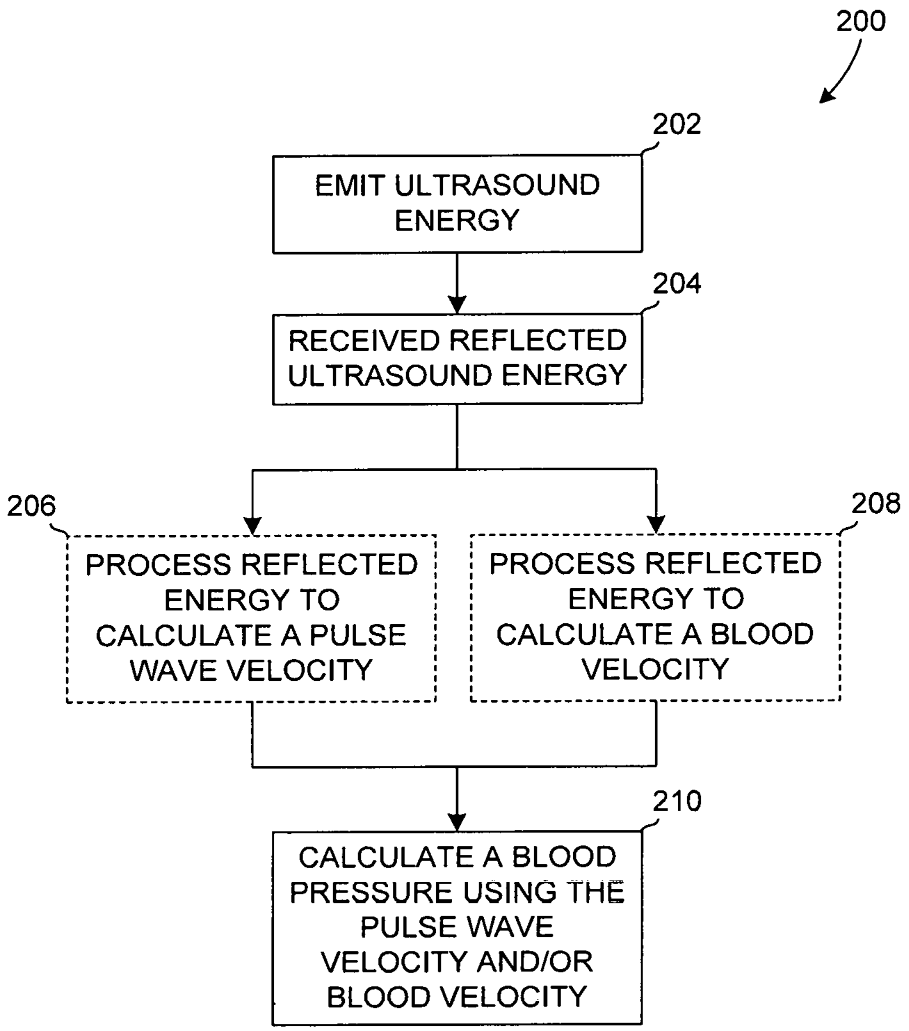
FIG. 2 is an example method non-invasive blood pressure measurement method.

FIG. 2 is an example method 200 for determining a blood pressure in a non-invasive manner. The method 200 uses pulse wave velocity (PWV) and/or blood velocity to determine/calculate a blood pressure. At 202, ultrasound energy is emitted, such as transmitted into tissues of the patient. Based on the reflectivity of the various tissues, through which the ultrasound energy transmits, ultrasound energy will reflect therefrom and be received at 204. Using the reflected ultrasound energy, a PWV can be calculated at 206 and/or a blood velocity can be calculated at 208. The calculations 206 and 208 can be made using one or more of the equations and/or methods described herein. Using one or more of the calculated values, a blood pressure can be calculated at 210. The calculated blood pressure can be output to a user, device and/or system and, optionally, used to assist with monitoring and/or treating a patient.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A non-invasive blood pressure (NIBP) device, comprising:
a transducer configured to:
emit ultrasound towards a blood vessel of a patient; and
detect a reflection of the ultrasound from the blood vessel; and
a processor configured to:
determine, by analyzing the reflection of the ultrasound, a change in a geometry of a radial cross section of a blood vessel caused by an ultrasound pulse;
determine a strain on the blood vessel caused by the ultrasound pulse by analyzing the change in the geometry of the radial cross-section of the blood vessel;
determine a Young's modulus of the blood vessel as a function of the stress on the blood vessel caused by the ultrasound pulse and the strain on the blood vessel caused by the ultrasound pulse; and
determine a blood pressure of the patient as a function of the Young's modulus and a velocity of blood flowing through the blood vessel.

2. The NIBP device of claim 1, wherein the transducer is further configured to:
emit the ultrasound pulse as an acoustic radiation force imaging (ARFI) pulse, and
wherein the processor is further configured to determine, by analyzing the reflection of the ultrasound, the stress on the blood vessel caused by the ultrasound pulse.

3. The NIBP device of claim 2, wherein the processor is configured to determine, by analyzing the reflection of the ultrasound, the stress on the blood vessel by determining an area over which the ultrasound pulse is applied to the blood vessel.

4. The NIBP device of claim 1, wherein the processor is configured to determine the Young's modulus further using a wall thickness of the blood vessel and a radius of the blood vessel.

5. The NIBP device of claim 1, wherein the processor is further configured to determine the velocity of the blood flowing through the blood vessel by analyzing the reflection of the ultrasound.

6. The NIBP device of claim 5, wherein the processor is configured to determine the velocity of the blood using a Doppler imaging technique.

7. The NIBP device of claim 5, wherein the processor is configured to determine the velocity of the blood using a vector velocity technique.

8. The NIBP device of claim 1, wherein the processor is further configured to:
determine the stress on the blood vessel caused by the ultrasound pulse by performing speckle tracking on the blood vessel.

9. The NIBP device of claim 3, wherein determining the area over which the ultrasound pulse is applied to the blood vessel comprises performing speckle tracking on the blood vessel.

10. The NIBP device of claim 1, wherein the geometry comprises a circumference of the radial cross-section of the blood vessel.

11. The NIBP device of claim 1, wherein the processor is further configured to:
determine a wall thickness of the radial cross-section of the blood vessel; and
determine a radius of the radial cross-section of the blood vessel, and
wherein the function of the Young's modulus and the velocity of blood flowing through the blood vessel is further dependent on the wall thickness and the radius.

12. The NIBP device of claim 1, further comprising:
an output device configured to output an indication of the blood pressure.

13. The NIBP device of claim 1, further comprising:
a power supply configured to provide power to the transducer and the processor; and
switching elements interconnecting the transducer with additional transducers.

14. A method, comprising:
emitting, by a transducer, ultrasound directed towards a blood vessel of a patient, the wave having energy;
detecting, by the transducer, a reflection of the ultrasound from the blood vessel;
determining, based on the reflection of the ultrasound, a change in a geometry of a radial cross-section of the blood vessel caused by an ultrasound pulse;
determining a strain on the blood vessel caused by the ultrasound pulse by analyzing the change in the geometry of the radial cross-section;
determining a Young's modulus of the blood vessel as a function of the strain on the blood vessel caused by the pulse and a stress on the blood vessel caused by the pulse; and
determining a blood pressure as a function of the Young's modulus and a velocity of blood flowing through the blood vessel.

15. The method of claim 14, wherein the ultrasound pulse comprises an acoustic radiation force imaging (ARFI) pulse, and
wherein the method further comprises determining the stress on the blood vessel caused by the pulse by:
determining a magnitude of force, caused by the ARFI pulse, applied to a wall of the blood vessel; and
determining an area over which the force is applied to the wall of the blood vessel.

16. The method of claim 14, further comprising:
determining, by analyzing the reflection of the ultrasound, the velocity of the blood flowing through the blood vessel by performing Doppler imaging or vector velocity imaging.

17. A method performed by a medical device, the method comprising:
determining a velocity of blood flowing through a blood vessel;
emitting, by a first transducer, ultrasound pulses toward the blood vessel;
determining an amount of force applied to the blood vessel by the ultrasound pulses;
determining an area over which the force is applied to the blood vessel by the ultrasound pulses;
determining a stress on the blood vessel as a function of the amount of force and the area over which the force is applied to the blood vessel by the ultrasound pulses;
emitting, by a second transducer, an ultrasound signal toward the blood vessel;
detecting, by the second transducer, a reflection of the ultrasound signal from the blood vessel;
determining, by analyzing the reflection of the ultrasound signal, a change in a circumference of a radial cross-section of the blood vessel caused by the ultrasound pulses;

determining a strain on the blood vessel as a function of the change in the circumference of the radial cross-section of the blood vessel and the circumference of the radial cross-section of the blood vessel;

determining a pulse wave velocity of the blood vessel as a function of the stress and the strain;

determining a blood pressure of the blood vessel by multiplying the velocity of the blood flowing through the blood vessel and the pulse wave velocity of the blood vessel; and outputting the blood pressure.

18. The method of claim 17, wherein determining the amount of force applied to the blood vessel by the ultrasound pulses comprises performing speckle tracking on the blood vessel and a surrounding tissue.

19. The method of claim 17, wherein determining the area over which the force is applied to the blood vessel by the ultrasound pulses comprises performing speckle tracking on the blood vessel.

* * * * *